United States Patent

Keller et al.

[11] Patent Number: 6,001,337
[45] Date of Patent: Dec. 14, 1999

[54] COSMETIC COMPOSITION WITH POLYMER-BOUND BENZOPHENONE CHROMOPHORES

[75] Inventors: Harald Keller, Ludwigshafen; Karin Sperling-Vietmeier; Horst Westenfelder, both of Neustadt, all of Germany

[73] Assignee: BASF Aktiengesellschaft, Ludwigshafen, Germany

[21] Appl. No.: 08/916,392

[22] Filed: Aug. 22, 1997

[51] Int. Cl.⁶ .................. A61K 31/765; C08F 220/10; C08F 8/14
[52] U.S. Cl. ............ 424/59; 424/78.21; 525/327.4; 525/340; 525/384; 525/385
[58] Field of Search .............. 424/401, 59, 78.21, 424/78.33; 525/327.4, 340, 384–385; 526/271

[56] References Cited

U.S. PATENT DOCUMENTS

| | | |
|---|---|---|
| 3,341,493 | 9/1967 | Goldberg . |
| 3,956,244 | 5/1976 | Carpenter et al. . |
| 4,522,807 | 6/1985 | Kaplan . |
| 4,980,412 | 12/1990 | Blum . |

FOREIGN PATENT DOCUMENTS

| | | |
|---|---|---|
| 60088066 | 10/1983 | Japan . |
| 89/04824 | 6/1989 | WIPO . |
| 96/14826 | 5/1996 | WIPO . |

OTHER PUBLICATIONS

CA 103: 161319 (1985).

*Primary Examiner*—Edward J. Webman
*Attorney, Agent, or Firm*—Keil & Weinkauf

[57] ABSTRACT

Cosmetic compositions contain a polymer with the repeating structural unit (I)

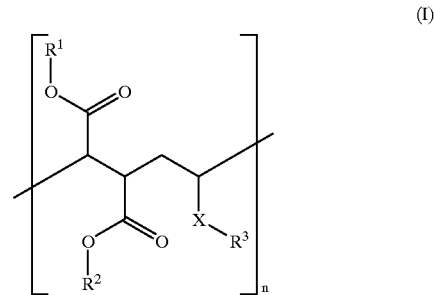

where the radicals have the meanings stated in the description.

3 Claims, No Drawings

COSMETIC COMPOSITION WITH POLYMER-BOUND BENZOPHENONE CHROMOPHORES

A cosmetic composition with polymer-bound benzophenone chromophores

The present invention relates to cosmetic compositions with polymer-bound benzophenone chromophores for protecting the skin and the hair from UV radiation.

It is frequently desirable for cosmetic sunscreen compositions which are applied to the skin to have good resistance to water. This property is particularly wanted when there is frequent contact of the skin with water or aqueous liquids such as perspiration. Polymers are frequently added to such compositions in order to obtain the required resistance to water.

Another possibility is to link the UV-absorbing groups covalently to a polymer.

WO89/4824 describes copolymers of the UV-absorbing styrene and maleic anhydride, vinylpyrrolidone or acrylates. These copolymers are very soluble in water and show little penetration into the skin.

JP 60/88066 describes UV-absorbing benzophenone derivatives which are linked via a urethane spacer to (meth)acrylates. These polymers are suitable as material for contact lenses and spectacle lenses.

Besides good resistance to water, the cosmetic compositions ought, however, to comply with a number of other properties such as little penetration into the skin, low content of residual monomers which must be avoided for toxicological and olfactory reasons, good processability, miscibility and stability with other components of cosmetic compositions.

We have found cosmetic compositions comprising a polymer with the repeating structural unit (I)

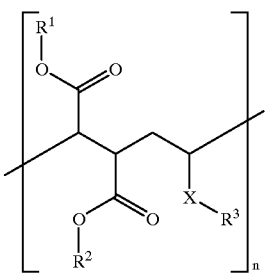

(I)

where
$R^1$ is

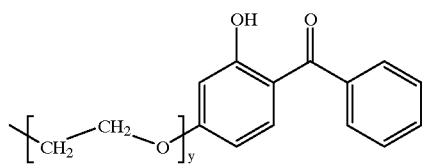

where y is 0–6,
$R^2$ is $R^1$, H, alkali metal, ammonium
$R^3$ is C3–C30-alkyl,—CO—R4 with
$R^4$ =C3–C30-alkyl
X is O or $CH_2$
n is 2–400.

The polymers for the cosmetic compositions according to the invention can be prepared by, in a first stage a) preparing a copolymer from maleic anhydride and an olefin of the formula (II)

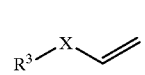

(II)

$R^3$ therein is C3—C30 alkyl, preferably C16—C22 alkyl, and X can be O or $CH_2$. Particularly preferred polymers are those with X=$CH_2$ and $R^3$=$C_{19}H_{39}$.

The polymerization is advantageously carried out by metering the maleic anhydride and an initiator separately into the olefin (II) at 80° to 150° C. under a protective gas. Initiators which can be used are the conventional azo initiators such as azoisobutyronitrile or peroxides such as dibenzoyl peroxide or tert-butyl 2-ethylperhexanoate in amounts of from 1 to 15%.

The copolymer obtained in a) is then reacted with the benzophenone derivative (III)

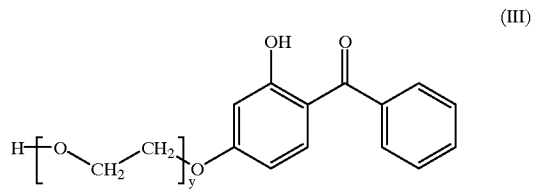

(III)

where y is 0–6. This entails cleavage of the anhydride linkage and bonding of the benzophenone derivative via an ester linkage to the polymer backbone.

Besides the benzophenone monomers it is possibly to include other vinylic comonomers such as vinylpyrrolidone, vinyl acetate, 1-olefins, acrylates and methacrylates in the polymer The benzophenone derivatives (III) are known or can be prepared by conventional methods from known starting compounds.

The polymer obtained in stage b) is then formulated with ancillary substances and additives which are conventional in cosmetics for the particular purpose. Examples of suitable ancillary substances and additives for sunscreen compositions are described by W. Umbach, Kosmetik, Georg-Thieme-Verlag Stuttgart, 1988.

The cosmetic compositions according to the invention are highly resistant to water and show good compatibility with skin and little penetration into the skin.

The invention is illustrated further by the following examples.

EXAMPLE 1

Preparation of a UV-Absorbing Polymer 200 g of an alternating copolymer of maleic anhydride and 1-olefin with a chain length of from $C_{20}$ to $C_{24}$, 203 g of 2-hydroxy-4 -(2-hydroxyethoxy)benzophenone and 4 g of polyphosphoric acid are stirred at 140° C. for 8 h. The reaction mixture is cooled to 60° C. and diluted with 350 ml of tetrahydrofuran. The polymer solution is then precipitated in 2.5 l of ethanol.

Yield: 244 g

Softening point: 49° C.

Molecular weight by GPC: Mn=5790, polydispersity=2.6

UV: 332 nm $E^1_1$=138

294 nm $E^1_1$=219

EXAMPLE 2

Preparation of a Sunscreen Composition

Phase A: 16 g of the polymer prepared in Example 1, 5 g of Finsolv® TN, 10 g of Witconol® APM and 0.5 g of Nip Nip, mixed at 60° C. and, after cooling, mixed with 1 g of Cremophor RH40.

Phase C: 0.3 g of Pemulen® TR1, 5 g of 1,2-propylene glycol and 65 g of water are mixed. Then 0.2 g of Tylose® H4000 is stirred in.

Phase A is stirred into Phase C and neutralized by adding 0.3 g of triethanolamine.

We claim:

1. A cosmetic composition comprising a polymer with the repeating structural unit (I)

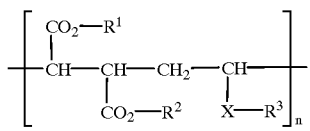

(I)

where $R^1$ is

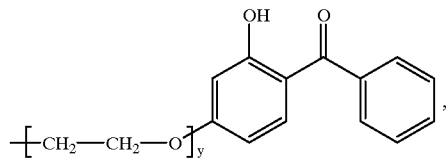

wherein y is 0 to 6, $R^2$ is hydrogen, an alkali metal ion, ammonium or a group as stated for $R^1$, $R^3$ is $C_{16}$–$C_{30}$-alkyl or —CO—$R^4$, wherein $R^4$ is $C_3$–$C_{30}$-alkyl, X is O or $CH_2$, and n is 2 to 400.

2. The cosmetic composition defined in claim 1, wherein $R^3$ is $C_{19}H_{39}$ and X is CH.

3. The cosmetic composition defined in claim 1, wherein $R^3$ is $C_{16}$–$C_{22}$-alkyl.

* * * * *

UNITED STATES PATENT AND TRADEMARK OFFICE
CERTIFICATE OF CORRECTION

PATENT NO.: 6,001,337

DATED: December 14, 1999

INVENTOR(S): KELLER et al.

It is certified that error appears in the above-identified patent and that said Letters Patent is hereby corrected as shown below:

Title page, insert the following at item

--[30]   Foreign Application Priority Data
Aug. 26, 1996   [DE]   Germany   196 34 399--

Signed and Sealed this

Twenty-second Day of August, 2000

Attest:

Q. TODD DICKINSON

Attesting Officer

Director of Patents and Trademarks